United States Patent
Abbadie et al.

(10) Patent No.: US 9,063,043 B2
(45) Date of Patent: Jun. 23, 2015

(54) ETCHING COMPOSITION, IN PARTICULAR FOR STRAINED OR STRESSED SILICON MATERIALS, METHOD FOR CHARACTERIZING DEFECTS ON SURFACES OF SUCH MATERIALS AND PROCESS OF TREATING SUCH SURFACES WITH THE ETCHING COMPOSITION

(75) Inventors: Alexandra Abbadie, Le Versoud (FR); Bernd Kolbesen, Taufkirchen (DE); Jochen Maehliss, Karlstein (DE)

(73) Assignee: SOITEC, Bernin (FR)

( * ) Notice: Subject to any disclaimer, the term of this patent is extended or adjusted under 35 U.S.C. 154(b) by 458 days.

(21) Appl. No.: 12/989,217

(22) PCT Filed: Apr. 24, 2009

(86) PCT No.: PCT/EP2009/003028
§ 371 (c)(1),
(2), (4) Date: Dec. 20, 2010

(87) PCT Pub. No.: WO2009/130050
PCT Pub. Date: Oct. 29, 2009

(65) Prior Publication Data
US 2011/0104905 A1 May 5, 2011

(30) Foreign Application Priority Data

Apr. 25, 2008 (EP) .................................... 08290398

(51) Int. Cl.
| | | |
|---|---|---|
| C09K 13/08 | (2006.01) | |
| C09K 13/00 | (2006.01) | |
| C09K 13/06 | (2006.01) | |
| H01L 21/302 | (2006.01) | |
| G01N 1/32 | (2006.01) | |

(Continued)

(52) U.S. Cl.
CPC *G01N 1/32* (2013.01); *C09K 13/04* (2013.01); *C09K 13/08* (2013.01); *H01L 21/67063* (2013.01)

(58) Field of Classification Search
None
See application file for complete search history.

(56) References Cited

U.S. PATENT DOCUMENTS

| | | | |
|---|---|---|---|
| 2,619,414 A | 11/1952 | Heidenreich | 41/42 |
| 2,827,367 A * | 3/1958 | Cox | 438/752 |
| 2003/0159362 A1* | 8/2003 | Singh et al. | 51/293 |

(Continued)

FOREIGN PATENT DOCUMENTS

| | | |
|---|---|---|
| CN | 101118855 | 2/2008 |
| EP | 1 734 572 A1 | 12/2006 |

(Continued)

OTHER PUBLICATIONS

A. Abbadie et al, "Study of HCl and Secco Defect Etching for Characterization of Thick sSOI", Journal of Electrochemical Society, vol. 154, No. 8 pp. H713-H719 (2007).

(Continued)

*Primary Examiner* — Shamim Ahmed
*Assistant Examiner* — Bradford Gates
(74) *Attorney, Agent, or Firm* — TraskBritt

(57) ABSTRACT

A chromium-free etching composition suitable for treating various silicon-containing surfaces, including strained silicon on insulator surfaces as well as stressed silicon surfaces. The etching composition invention includes hydrofluoric acid, nitric acid, acetic acid and an alkali iodide, preferably potassium iodide, present in an amount of 1 mmol/100 ml or more.

18 Claims, 2 Drawing Sheets

Etching rates as a function of KI concentration for a solution with volume ratios 1/32.4/34.

(51) Int. Cl.
    *C09K 13/04*     (2006.01)
    *H01L 21/67*     (2006.01)

(56) References Cited

U.S. PATENT DOCUMENTS

2007/0204789 A1    9/2007    Sato .................. 117/14
2008/0069756 A1    3/2008    Kume ................ 423/348

FOREIGN PATENT DOCUMENTS

| | | |
|---|---|---|
| EP | 1 852 905 A1 | 11/2007 |
| JP | 57-172738 | 10/1982 |
| JP | 01-214026 | 8/1989 |
| JP | 2003-209150 | 7/2003 |
| JP | 2004-235350 | 8/2004 |
| JP | 2004-349420 | 12/2004 |
| JP | 2005-285987 | 10/2005 |

OTHER PUBLICATIONS

International Search Report, PCT/EP2009/003028, mailed Jun. 16, 2009.
W.C. Dash, "Copper Precipitation on Dislocations in Silicon;" Journal of Applied Physics, vol. 27, No. 10, pp. 1193-1195 (1956).
F. Secco d'Aragona, "Dislocation Etch for (100) Planes in Silicon" J. Electrochem. Soc, vol. 119, No. 7, pp. 948-951 (1972).

* cited by examiner

Etching rates as a function of KI concentration for a solution with volume ratios 1/32.4/34.

Etch rates as a function of $HNO_3$ volume ratio (/HF) for a solution $HF/HNO_3/CH_3COOH$ + KI = 6 mmol à 100 ml sol.

SF number correlation between a Cr-free etch containing KI and Secco for sSOI and sSi/SiGe wafers.

SF length correlation between a Cr-free etch containing KI and Secco for various wafers

ETCHING COMPOSITION, IN PARTICULAR FOR STRAINED OR STRESSED SILICON MATERIALS, METHOD FOR CHARACTERIZING DEFECTS ON SURFACES OF SUCH MATERIALS AND PROCESS OF TREATING SUCH SURFACES WITH THE ETCHING COMPOSITION

CROSS-REFERENCE TO RELATED APPLICATION

This application is a 371 filing of International Patent Application PCT/EP2009/003028, filed Apr. 24, 2009.

BACKGROUND

The present invention relates to a method for characterizing defects on silicon-surfaces, in particular stressed or strained silicon-surfaces, a method for treating silicon-surfaces with the etching solution and the etching solution to be employed in the method and process of the present invention.

Particularly, the present invention relates to the revelation of stacking faults and/or dislocations that can be present in thin semiconductor films.

PRIOR ART

Crystalline defects in substrate for microelectronic devices are highly undesirable as they have a negative impact on the functionality and reliability of integrated circuits, formed using the substrates, such as wafers, in particular silicon-on-insulator (SOI) type wafers. The typical approach for identifying crystalline defects and thereby characterizing the quality of substrate surfaces is the use of so-called structural etching solutions. These etching solutions enable the decoration of crystalline defects, since crystalline defects give rise to either hillocks or etch pits after application of the structural etching solution.

Various etching solutions have been proposed for silicon surfaces that require typically the presence of strong oxidants.

F. Secco describes in Journal of Electrochemical Society, 119, no. 7, pp. 948-951 (1972) an etching solution for revealing etch pits in silicon, consisting of a mixture of hydrofluoric acid and aqueous alkali dichromate. The alkali chromate acts as oxidizing agent while the hydrofluoric acid dissolves the oxidation product, namely silicon dioxide. However, chromates and, in particular, dichromates are highly toxic due to their ability to interact with cells and DNA.

W. C. Dash in the Journal of Applied Physics, vol. 27, no. 10, pp. 1193-1195 (1956) discloses a further etched solution able to reveal defects on semiconductor substrates, consisting of hydrofluoric acid, nitric acid and acetic acid. While this solution is able to etch semiconductor substrates, including silicon substrates, the etching solution according to Dash is not able to differentiate between different types of defects and furthermore does not provide a satisfactory etch rate.

U.S. Pat. No. 2,619,414 discloses a further chemical etchant to be applied on semiconductor surfaces to improve their electrical characteristics. The chemical etchant disclosed in U.S. Pat. No. 2,619,414 comprises acetic acid, nitric acid, hydrofluoric acid and bromine. The drawback of the composition as disclosed in U.S. Pat. No. 2,619,414 is the use of bromine, which is highly instable and volatile, so that the chemical etchant according to this prior art reference can only be stored for a very short time in the dark at low temperatures and can be handled only under ventilation, since bromine evaporates from the composition. Although bromine is not as toxic as chromate or dichromate, precautionary measures nevertheless have to be taken when using the chemical etchant according to U.S. Pat. No. 2,619,414.

EP 1734572 relates to a method of evaluating crystal defects on a silicon wafer having a low electrical resistivity with a chromium-free etching solution. The etching solution is comprised of hydrofluoric acid, nitric acid, acetic acid, water and preferably potassium iodide.

JP 2004-235350 describes a method of etching of an SOI wafer for the evaluation of crystal defects using an etching solution comprising hydrofluoric acid, nitric acid, acetic acid, water and preferably potassium iodide.

JP 2003-209150 relates to a method for detecting a crystal defect that degrades the electrical property of a semiconductor device. The etching solution used for the detection is comprised of hydrofluoric acid, nitric acid, acetic acid, water and iodine or iodide.

EP 1852905 discloses an etching method for a silicon single crystal having a low electrical resistivity. The etching solution in accordance with EP 1852905 comprises hydrofluoric acid, nitric acid, acetic acid, water and preferably potassium iodide having an etching rate of higher than 0.1 µm/min and is in particular effective for detecting bulk micro defects (BMDs). However, these etching solutions enable the detection of BMDs, but are not able to detect defects such as dislocation and stacking faults, which are characterized by different activation energies and a lower strain field.

In addition, novel silicon containing materials have been developed and have found their field of application, requiring a further adaptation and adjustment of the chemicals used for treating silicon-containing surfaces. Representative examples of such novel silicon-containing materials are strained silicon on insulator type wafers, i.e., materials for which all known etching compositions are not suitable and furthermore materials that show novel types of defects that need to be revealed.

SUMMARY OF THE INVENTION

In view of the progress in semiconductor industry, involving in particular the decrease of the minimum feature sizes used to fabricate integrated circuits, the introduction of new substrate materials, such as silicon-on-insulator (SOI) or strained-silicon-on-insulator (sSOI), improved methods for quality characterization are required, in particular with respect to the following features:

Satisfactory etch rates, so that even thin substrates can be etched with a sufficient control of etch rate/etch time/removed surface thickness.

Etch sensitivity, i.e., the possibility to detect different types of defects (such as D defects corresponding to agglomerates of vacancies and oxygen precipitates), most preferably identifying different types of defects after one type of etching treatment, in particular to detect dislocation and/or stacking faults.

Reduction of health risks and environmental problems by using suitable components for the etching composition, without sacrificing the desired properties, etch rate, etch sensitivity, etc.

Stability of the etching composition, so that same can be stored for a certain period of time and can be handled without highly elaborated safety measures.

The present invention now provides a new etching solution comprising a solution of HF, $HNO_3$, acetic acid and an alkali iodide, wherein the alkali iodide is present in an amount of 1 mmol/100 ml or more. The present invention furthermore provides a method for characterizing defects on silicon surfaces comprising the step of treating the silicon surface with an etching solution as described herein. Finally, the present invention provides a process for etching silicon surfaces comprising the step of treating the silicon surface with an etching solution as disclosed herein.

Further preferred embodiments for all aspects of the present invention are also explained in the following description.

DETAILED DESCRIPTION OF THE PRESENT INVENTION

Figure 1:
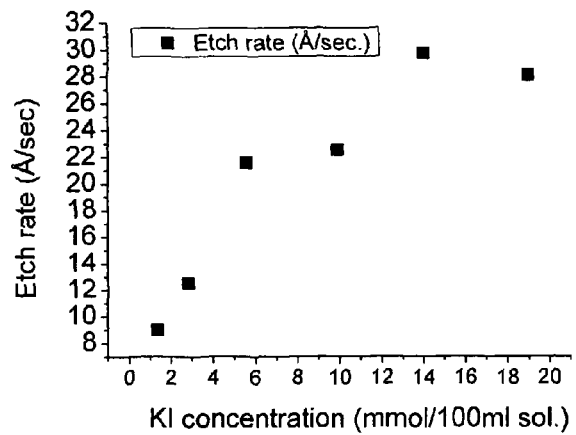
FIG. 1 shows the correlation between etch rate and potassium iodide concentration in the etching solution in accordance with the present invention.

The present invention will be first described in connection with the etching solution. The preferred embodiments discussed herebelow, however, also apply with respect to the methods of the present invention, unless otherwise stated.

The present invention is mainly characterized in that a novel etching solution for treating semiconductor surfaces is provided. The etching solution in accordance with the present invention comprises hydrofluoric acid, nitric acid, acetic acid, and an alkali iodide, preferably potassium iodide. The components of the etching solution in accordance with the present invention are explained in further detail below:

1.) The hydrofluoric acid to be employed in accordance with the present invention preferably is an aqueous solution of HF with a concentration of above 30%, preferably above 40%, more preferably above 45%, such as about 49%.
2.) Furthermore, the etching solution in accordance with the present invention comprises nitric acid. The nitric acid to be employed in accordance with the present invention again preferably is an aqueous solution, typically showing a nitric acid concentration of above 50%, more preferably above 60%, and in particular above 65%, such as about 70%.
3.) The acetic acid to be employed in accordance with the present invention preferably is a pure acetic acid, such as an acetic acid commercially available as glacial acetic acid having an acetic acid content of 99%.
4.) The alkali iodide preferably is potassium iodide and typically is employed in the form of an aqueous solution. In another embodiment the alkali iodide, preferably potassium iodide is employed as a solid.

Preferably the etching solution in accordance with the present invention consists of the components identified above, i.e., the etching solution is an aqueous mixture, preferably solution, of the components mentioned above.

These components of the etching solution in accordance with the present invention may be present in the overall mixture in the following amounts:

Acetic acid: 20 to 90 vol. %, based on the overall composition of the etching solution, preferably 30 to 90 vol. %, more preferably 50 to 90 vol. %, calculated on the basis of an acetic acid having a concentration of 99%.

Hydrofluoric acid: 1 to 30 vol. %, preferably 1 to 5 vol. %, calculated on the basis of an aqueous HF having a concentration of 49% (referring to aqueous HF having a concentration of 49%, commercially available).

Nitric acid: addition amounts so that the volumic ratio $HF/HNO_3$ is from 1:2 to 1:50, preferably 1:5 to 1:40, more preferably 1:8 to 1:35, in particular 1:8. In another preferred embodiment, the volumic ratio $HF/HNO_3$ is 1:32, in each case calculated on the basis of an aqueous HF having a concentration of 49% and an aqueous nitric acid having a concentration of 70%, respectively (referring to aqueous HF having a concentration of 49%, commercially available, and aqueous nitric acid having a concentration of 70%, commercially available).

Ratio $HF/CH_3COOH$: preferably adjusted to a volumic ratio from 1:2 to 1:50, preferably 1:5 to 1:40, more preferably 1:8 to 1:35 in particular 1:8. In another preferred embodiment, the volumic ratio $HF/CH_3COOH$ is 1:35, in each case calculated on the basis of an aqueous HF having a concentration of 49% and glacial acetic acid having an acetic acid content of 99%, respectively (referring to aqueous HF having a concentration of 49%, commercially available, and glacial acetic acid having an acetic acid content of 99%, commercially available).

Alkali iodide: molar concentration 1 mmol/100 ml or more, preferably 1 to 30 mmol/100 ml. In one embodiment the molar concentration is preferably 2 to 30 mmol/100 ml, more preferably 5 to 20 mmol/100 ml, in particular 5.5 to 18 mmol/100 ml. In another embodiment, the molar concentration is preferably 1 to 12 mmol/100 ml, more preferably 1 to 5 mmol/100 ml, in particular 1 to 1.8 mmol/100 ml.

When potassium iodide is used as the alkali iodide, the concentration is 1.6 g/l or more, preferably 1.6 to 48 g/l. In one preferred embodiment, the concentration is preferably 3.2 to 48 g/l, more preferably 8 to 32 g/l, in particular 8.8 to 28.8 g/l. In another embodiment, the concentration is preferably 1.6 to 19 g/l, more preferably 1.6 to 8 g/l, in particular 1.6 to 3 g/l.

The etching solution in accordance with the present invention may be prepared by simply mixing the components identified above in the desired ratio, typically using conventional safety measures. The order of addition of the components is not critical and the components usually are mixed within a stirred vessel. The composition as obtained may be stored without loss of etching activity for several days, typically under cooling conditions.

The use of an etching solution in accordance with the above is highly satisfactory. The etching solution as defined above provides for an etch rate that is low enough so that even thin semiconductor substrates can be etched, without sacrificing the desired etching properties, such as formation of well-developed etch pits, facilitating the surface characterization. Due to the relative high acetic acid content in the preferred etching solution in accordance with the present invention, highly satisfactory homogeneous surfaces can be obtained and the use of alkali iodide enables, as discussed herein the treatment of a very broad variety of silicon containing surfaces.

Further, the etching solution in accordance with the present invention is particularly used for SOI-like substrates. SOI-like structures are characterized by a buried insulator layer that is modifying the surface state of the top semiconductor material. The electrical charges repartition at the surface of an SOI structure is different from the electrical charge repartition at the surface of a bulk, massive silicon surface, since a residual charge of the buried insulator may attract/repel charges in the fine semiconductor layer. As a consequence, it is more difficult to initiate the chemical etching reaction of the etchant on the semiconductor material, in particular when the etchant is used to reveal defects such as dislocation and/or stacking faults, which are characterized by different activation energies and a lower strain field. When using an etching solution in accordance with the present invention comprising potassium iodide in an amount of from 1 to 30 mmol/100 ml, the etching reaction is initiated and the etching rate can be precisely controlled to allow a precise detection of defects, in particular defects like dislocation and/or stacking faults. If the amount of potassium iodide is more than 30 mmol/100 ml, the etching rate increases and control of etching will be more difficult. If the amount of potassium iodide is lower than 1 mmol/100 ml, the etching reaction might be difficult to initiate.

Figure 2:
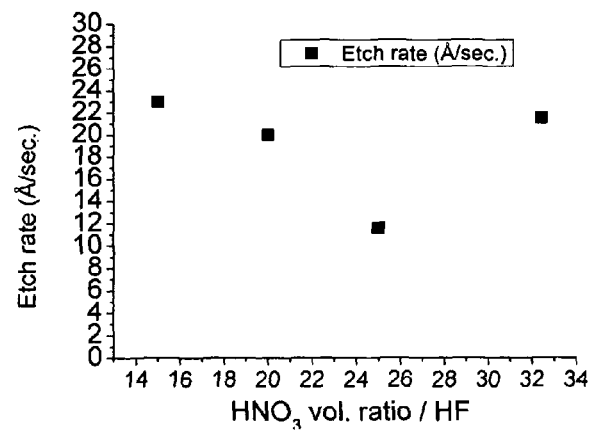
FIG. 2 displays the dependency of etch rate from the volume ratio of nitric acid to hydrofluoric acid.

FIG. 1 displays experimental results for etching rates with a volume ratio as defined above of hydrofluoric acid:nitric acid:acetic acid of 1:32.4:34.6 for varying potassium iodide concentrations. FIG. 1 shows that with increasing potassium iodide concentrations etching rates can be adjusted in order to obtain an increase of the etching rate of from about 9 to approximately 30 Å/sec. FIG. 2 on the other hand displays the result as obtained for etching compositions in accordance with the present invention with a potassium iodide concentration of 6 mmol/100 ml and varying ratios of nitric acid: hydrofluoric acid, with a constant ratio of acetic acid. FIG. 2 shows that relatively stable etching rates are obtained over a broad range of ratios of nitric acid to hydrofluoric acid. It shows as well that an optimum in the etch rate is obtained for a volume ration of $HNO_3$ ratios (versus HF) of below 15.

Figure 3:
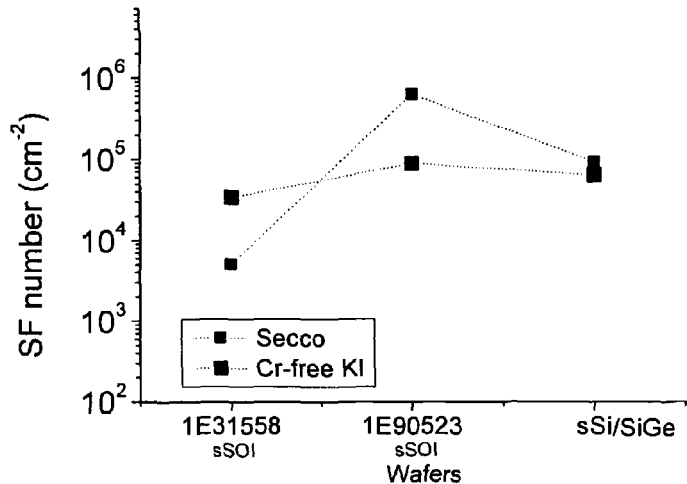
FIG. 3 shows results concerning dislocation densities as obtained with the etching solution in accordance with the present invention, compared with a typical example of a prior art etching solution according to Secco.
Figure 4:
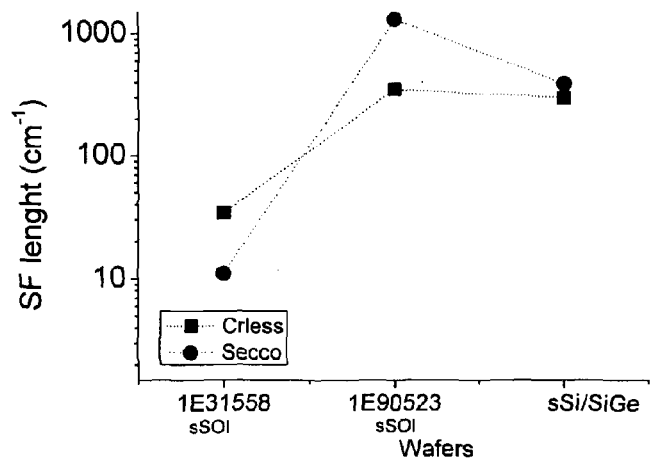
FIG. 4 shows a similar comparison between results obtained when using the etching solution in accordance with the present invention and prior art reference etching composition according to Secco.

FIG. 3 then displays the comparison between an etching composition in accordance with the present invention and the prior art etching composition according to Secco, for different types of silicon-containing surfaces. A similar correlation is given in FIG. 4, which likewise discloses results on silicon-containing surfaces with respect to the defects revealed. The defects as evaluated in the experiments displayed in FIGS. 3 and 4 are stacking faults (SF). The results as can be derived from FIGS. 3 and 4 clearly show that the etching composition in accordance with the present invention, despite not containing the chromium containing component reported to be essential in the prior art, shows highly satisfactory and reliable results, comparable to the results as achieved with the prior art Secco composition.

With an etching solution in accordance with the present invention, it is possible to reveal surface defects on semiconductor substrates, even on thin substrates, such as SOI or sSOI substrates. The shape of revealed etch pits are either conic shallow pits and observable as round mark (spot) after etching treatment, either linear defects or stacking faults (observable as lines after etching). The etching solution in accordance with the present invention, depending from the actual composition, provides, for example, etch rates of 3 to 70 Å/sec, with the possibility to adjust etch rates as desired, for example from 10 to 40 Å/sec, so that highly satisfactory total etch times can be achieved even when using thin substrates, such as SOI or sSOI substrates where it is required to remove only 100 to 500 Å of the initial surface.

In particular, the etching solution in accordance with the present invention is efficient to reveal stacking faults and/or dislocations in thin semiconductor films. A precise control of the etching rate and, thus, a precise detection of defects, in particular defects in thin semiconductor films, is provided. For example, the thin semiconductor films are preferably films of the SOI type having a top silicon layer below 1000 Å, strained silicon substrates having a top silicon layer typically between 200 and 800 Å or strained silicon germanium layers. Further, defects on structures comprising bilayers of silicon layers or silicon germanium layers (which each may be strained layers) can be revealed with the etching solution in accordance with the present invention. Generally, the strain can be compressive or tensile.

Preferably, the etching solution in accordance with the present invention provides an etching rate of below 30 Å/sec, more preferably below 25 Å/sec.

The etching solution in accordance with the present invention preferably does not contain any additional water besides the water introduced with the components of the etching composition, such as hydrofluoric acid, nitric acid, and acetic acid.

In this respect, it furthermore has been shown, using the etching solution in accordance with Secco (see above) as reference, that the solution in accordance with the present invention enables a highly satisfactory and reliable identification of defects, as evidenced by the very similar defects densities obtained (for example, SF numbers as shown in FIGS. 3 and 4).

Overall, it is therefore readily apparent that the etching solution in accordance with the present invention enables a vast improvement compared with the etching compositions as known so far from the prior art.

Surprisingly, it has been found in addition that by using a composition for the etchant comprising hydrofluoric acid, nitric acid, acetic acid and preferably potassium iodide, various defects, including dislocations and stacking faults can be revealed not only on conventional silicon surfaces, but also on strained and stressed surfaces, such as strained SOI layers or stressed Si layers grown on top of SiGe layers, being stressed due to the percentage of the germanium content in the underlying layer. The present invention provides highly satisfactory results, accordingly, not only on conventional silicon surfaces, but also on those specific types of silicon surfaces, A further preferred embodiment of the present invention is, in addition, the use of an additional treatment with hydrofluoric acid, after treating the silicon surface with the etchant in accordance with the present invention (and usual intermediate treatments, such as rinsing the treated surface with deionized water). By applying such a further treatment using hydrofluoric acid, new types of dislocations can be detected, defects that are normally only detected with a treatment using gaseous HCl, accordingly problematic material. The new defects that can be detected by using this additional treatment are dislocations present at the intersection of two stacking faults, defects that can be only detected to a lesser degree with the conventional etchant compositions known from the prior art, such as the above-described Secco etchant.

Further, the present invention provides the advantage that without sacrificing the EPD, the reliability of the etching process, the etching solution in accordance with the present invention may be employed at rather low temperatures with highly efficient etching results, so that a further control of the etching process is enabled. Due to the rather low etching rates at low temperature, it is in particular possible to etch, with a sufficiently high degree of control, very thin substrates without endangering the overall integrity of the substrate to be treated.

It is accordingly possible to conduct etching over a wide range of temperatures, such as from 5° C. to 50° C., preferably 5° C. to 25° C., and depending from the circumstances either at low temperatures such as from 5° C. or 8° C. to 15° C., or at higher temperatures, such as from 20° C. to 25° C., in embodiments 23° C.

Further, as already outlined above, the present invention provides a method for characterizing defects on silicon surfaces as well as a process for etching silicon surfaces, which both comprise a step of etching a silicon surface with an etching solution as defined herein.

In the method as well as the process in accordance with the present invention the silicon surfaces may be surfaces of semiconductor substrates, such as conventional silicon substrates or preferably SOI or sSOI materials or even stressed Si surfaces.

These substrates may be subjected to any conventional pretreatment, and after application of the etching solution in accordance with the present invention, the substrates again may be subjected to conventional post-treatments such as washing, drying, etc., as required.

As indicated above, the use of the etching solution in accordance with the present invention enables a superior control of the etch rate together with highly satisfactory etch results, i.e., highly reliable detection of defects on the treated surface.

The present invention accordingly proves that it is possible to use the etching solution that has been described in an industrial etching process in replacement of the reference Secco solution.

What is claimed is:

1. An etching solution consisting of HF, $HNO_3$, acetic acid, and potassium iodide in an amount of from 1 to 12 mmol/100 ml, wherein the HF and $HNO_3$ are present in a volume ratio of from 1:8 to 1:35, the HF and acetic acid are present in a volume ratio of from 1:8 to 1:35 and the acetic acid is present in an amount of 50 to 90 vol. %, wherein the solution does not contain any additional water besides the water introduced with the acids.

2. The etching solution of claim 1, wherein the potassium iodide is present in an amount of from 1 to 5 mmol/100 ml.

3. The etching solution of claim 1, wherein the HF and $HNO_3$ are present in a volume ratio of 1:8 or 1:32.

4. The etching solution claim 1, wherein the HF and acetic acid are present in a volume ratio of 1:8 or 1:35.

5. The etching solution of claim 1, wherein the solution has a temperature of from 5° C. to 25° C. and a volume ratio of hydrofluoric acid:nitric acid:acetic acid of 1:32.4:34.6.

6. The etching solution of claim 1, wherein the acetic acid has a concentration of 99% and is present in an amount of 50 to 90 vol. %, the HF has a concentration of 49% and is present in an amount of 1 to 30 vol. %, and the $HNO_3$ has a concentration of 70%.

7. The etching solution according to claim 1, wherein the acetic acid has a concentration of 99%, the HF is aqueous HF having a concentration of 49% and is present in an amount of 1 to 30 vol. %, and the $HNO_3$ has a concentration of 70%.

8. A method for characterizing defects on silicon surfaces, comprising the step of treating the silicon surface with an etching solution according to claim 1.

9. The method of claim 8, wherein the silicon surface is a SOI or sSOI substrate or a stressed Si surface on a SiGe layer.

10. The method of claim 8, which further comprises a post-treatment of the treated silicon surface with HF.

11. The method of claim 8, which further comprises one or more of the following processes conducted prior to the characterizing of defects:
pretreatment of the silicon surface with HF;
intermittent treatments of the silicon surface by rinsing with deionized water; and drying of the silicon surface.

12. The method of claim 8, which further comprises visually evaluating the treated silicon surface.

13. The method of claim 8, wherein the step of treating the silicon surface with an etching solution is conducted at a temperature of from 5° C. to 25° C.

14. A process for etching silicon surfaces, comprising the step of treating the silicon surface with an etching solution according to claim 1.

15. The process of claim 14, wherein the silicon surface is a SOI or an sSOI substrate or a stressed Si surface on a SiGe layer.

16. The process of claim 14, further comprising a pretreatment of the silicon surface with HF.

17. The process of claim 14, further comprising a post-treatment of the silicon surface by rinsing with deionized water and dipping in a HF 49% solution for a few seconds to further delineate defects.

18. The process of claim 14, wherein the step of treating the silicon surface with an etching solution is conducted at a temperature of from 5° C. to 25° C.

* * * * *

UNITED STATES PATENT AND TRADEMARK OFFICE
CERTIFICATE OF CORRECTION

PATENT NO. : 9,063,043 B2  
APPLICATION NO. : 12/989217  
DATED : June 23, 2015  
INVENTOR(S) : Alexandra Abbadie, Bernd Kolbesen and Jochen Maehliss Page 1 of 1

It is certified that error appears in the above-identified patent and that said Letters Patent is hereby corrected as shown below:

In the claims:
CLAIM 4, COLUMN 7, LINE 40, change "solution claim" to --solution of claim--

Signed and Sealed this  
Fifth Day of January, 2016

Michelle K. Lee  
*Director of the United States Patent and Trademark Office*